US007528131B2

(12) United States Patent
Persichetti et al.

(10) Patent No.: US 7,528,131 B2
(45) Date of Patent: May 5, 2009

(54) SUBSTITUTED MORPHOLINYL COMPOUNDS

(75) Inventors: Rose A. Persichetti, Stow, MA (US); Scott L. Harbeson, Cambridge, MA (US)

(73) Assignee: Concert Pharmaceuticals Inc., Lexington, MA (US)

( * ) Notice: Subject to any disclaimer, the term of this patent is extended or adjusted under 35 U.S.C. 154(b) by 0 days.

(21) Appl. No.: 12/106,127

(22) Filed: Apr. 18, 2008

(65) Prior Publication Data

US 2008/0261983 A1 Oct. 23, 2008

Related U.S. Application Data

(60) Provisional application No. 60/912,807, filed on Apr. 19, 2007.

(51) Int. Cl.
*A61K 31/5375* (2006.01)
*C07D 265/30* (2006.01)
(52) U.S. Cl. ............... 514/237.8; 544/106; 544/162; 514/231.2
(58) Field of Classification Search ............... 544/106, 544/162; 514/231.2, 237.8
See application file for complete search history.

(56) References Cited

U.S. PATENT DOCUMENTS

| 5,304,121 | A | 4/1994 | Sahatjian |
| 5,886,026 | A | 3/1999 | Hunter et al. |
| 6,099,562 | A | 8/2000 | Ding et al. |
| 6,676,933 | B2 | 1/2004 | Vergez et al. |
| 6,803,031 | B2 | 10/2004 | Rabinowitz et al. |
| 7,014,866 | B2 | 3/2006 | Infeld et al. |
| 2005/0239845 | A1 | 10/2005 | Proehl et al. |
| 2006/0079502 | A1 | 4/2006 | Lang |
| 2006/0094744 | A1 | 5/2006 | Maryanoff et al. |

FOREIGN PATENT DOCUMENTS

| EP | 243 959 | 8/1992 |
| WO | WO 2005/004865 | 1/2005 |
| WO | WO 2006/011159 | 2/2006 |

OTHER PUBLICATIONS

Fisher et al., "The complexities inherent in attempts to decrease drug clearance by blocking sites of CYP-mediated metabolism," *Curr. Opin. Drug Disc. Dev.*, 2006, 9:101-109.
Freireich et al., "Quantitative comparison of toxicity of anticancer agents in mouse, rat, hamster, dog, monkey, and man," *Cancer Chemother. Rep.*, 1966, 50:219-244.
Gannes et al., "Natural abundance variations in stable isotopes and their potential uses in animal physiological ecology," *Comp. Biochem. Physiol. Mol. Integr. Physiol.*, 1998, 119:725-737.
Houston, "Utility of in vitro drug metabolism data in predicting in vivo metabolic clearance," *Biochem. Pharmacol.*, 1994, 47:1469-1479.

Houston et al., "Prediction of hepatic clearance from microsomes, hepatocytes, and liver slices," *Drug Metab Rev.*, 1997, 29:891-922.
Iwatsubo et al., "Prediction of in vivo drug metabolism in the human liver from in vitro metabolism data," *Pharmacol. Ther.*, 1997, 73:147-171.
Kato et al., "Synthesis and biological activities of metabolites of mosapride, a new gastroprokinetic agent," *Chem. Pharm. Bull.*, 1995, 43(4):699-702.
Kato et al., "Novel benzamides as selective and potent gastric prokinetic agents. 1. Synthesis and structure-activity relationships of N-[(2-morpholinyl)alkyl]benzamides," *J. Med. Chem.*, 1990, 33(5):1406-1413.
Kato et al., "Novel benzamides as selective and potent gastrokinetic agents. 2. Synthesis and structure-activity relationships of 4-amino-5-chloro-2-ethoxy-N-[[4-(4-fluorobenzyl)-2-morpholinyl]methyl] benzamide citrate (AS-4370) and related compounds," *J. Med. Chem.*, 1991, 34(2):616-624.
Lave et al., "The use of human hepatocytes to select compounds based on their expected hepatic extraction ratios in humans," *Pharm. Res.*, 1997, 14:152-155.
Morie et al., "Synthesis and biological activities of the optical isomers of (+/−)-4-amino-5-chloro-2-ethoxy-N-[[4-(4-fluorobenzyl)-2-morpholinyl]methyl]benzamide (mosapride)," *Chem. Pharm. Bull.*, 1994, 42(4):877-882.
Obach, "Predictions of human clearance of twenty-nine drugs from hepatic microsomal intrinsic clearance data: An examination of in vitro half-life approach and nonspecific binding to microsomes," *Drug Metab. Disp.*, 1999, 27:1350-1359.
Scientific Tables, 1970, Geigy Pharmaceuticals, Ardsley, N.Y., p. 537.
Wada and Hanba, "Natural abundance of carbon, nitrogen, and hydrogen isotope ratios in biogenic substances: present and future," *Seikagaku*, 1994, 66:15-29 (English portions included).
Armstrong et al., "Measurement of $5\text{-HT}_4$ receptor-mediated esophageal responses by digital sonomicrometry in the anesthetized rat," *J. Pharmacol. Toxicol. Meth.*, 2006, 53:198-205.
Foster, "Deuterium Isotope Effects in the Metabolism of Drugs and Xenobiotics: Implications for Drug Design," *Adv. Drug Res.*, 1985, 14:1-40.
Kato and Hirokawa, "Synthesis of Deuterated Mosapride Citrate," *J. Labelled Comp. Radiopharmaceut.*, 1995, 36(10):927-932.
Kushner et al., "Pharmacological uses and perspectives of heavy water and deuterated compounds," *Can. J. Physiol. Pharmacol.*, 1999, 77:79-88.

*Primary Examiner*—Golam M Shameem
(74) *Attorney, Agent, or Firm*—Fish & Richardson P.C.

(57) ABSTRACT

This disclosure relates to novel substituted morpholinyl compounds and their derivatives, pharmaceutically acceptable salts, solvates, and hydrates thereof. This disclosure also provides compositions comprising a compound of this disclosure and the use of such compositions in methods of treating diseases and conditions that are beneficially treated by administering a 5HT4 serotonin receptor agonist.

11 Claims, No Drawings

SUBSTITUTED MORPHOLINYL COMPOUNDS

CROSS-REFERENCE TO RELATED APPLICATION

This application claims priority under 35 U.S.C. § 119 to U.S. Provisional Application Ser. No. 60/912,807, filed Apr. 19, 2007, the entire contents of which are incorporated by reference herein.

This disclosure relates to novel substituted morpholinyl compounds and their derivatives, pharmaceutically acceptable salts, solvates, and hydrates thereof. This disclosure also provides compositions comprising a compound of this disclosure and the use of such compositions in methods of treating diseases and conditions that are beneficially treated by administering a 5HT4 serotonin receptor agonist.

Mosapride is known as Gasmotin® and by the chemical name (+/−)-4-Amino-5-chloro-2-ethoxy-N-[4-fluorobenzyl)-morpholino-2-ylmethyl]benzamide citrate dihydrate.

Mosapride stimulates serotonin-5-HT4 receptors in the gastrointestinal nerve plexus, which increases the release of acetylcholine, resulting in enhanced gastrointestinal motility and gastric emptying.

Mosapride is currently approved in the Far East for treatment of gastrointestinal symptoms associated with chronic gastritis including heartburn; nausea; vomiting; and gastroesophageal reflux disease (GERD). Mosapride is also in Phase II clinical trials for the treatment of GI dumping syndrome or post-gastrectomy syndrome. Additional clinical studies have been initiated using mosapride for treating constipation in patients with Parkinson's disease; treating patients with type-2 diabetes mellitus in order to improve insulin action; treating patients with gastroparesis; and treatment of patients with opiate-induced respiratory depression.

Despite the beneficial activities of mosapride, there is a continuing need for new compounds to treat the aforementioned diseases and conditions.

DEFINITIONS

The terms "ameliorate" and "treat" are used interchangeably and include therapeutic and/or prophylactic treatment. Both terms mean decrease, suppress, attenuate, diminish, arrest, or stabilize the development or progression of a disease (e.g., a disease or disorder delineated herein).

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of mosapride will inherently contain small amounts of deuterated isotopologues. The concentration of naturally abundant stable hydrogen and carbon isotopes, notwithstanding this variation, is small and immaterial as compared to the degree of stable isotopic substitution of compounds of this disclosure. See, for instance, Wada E et al., Seikagaku 1994, 66:15; Ganes L Z et al., Comp Biochem Physiol Mol Integr Physiol 1998, 119:725. In a compound of this disclosure, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in the compound.

The term "isotopic enrichment factor" as used herein means the ratio between the isotopic abundance and the natural abundance of a specified isotope.

In other embodiments, a compound of this disclosure has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

The term "isotopologue" refers to a species that has the same chemical structure and formula as a specific compound of this invention, with the exception of the isotopic composition at one or more positions, e.g., H vs. D. Thus an isotopologue differs from a specific compound of this invention in the isotopic composition thereof.

The term "compound," as used herein, is also intended to include any salts, solvates or hydrates thereof.

A salt of a compound of this disclosure is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, mal onate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present may contain an asymmetric carbon atom, for example, as the result of deuterium substitution or otherwise. As such, compounds of this disclosure can exist as either individual enantiomers, or mixtures of the two enantiomers. Accordingly, a compound of the present disclosure will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium.

"Stereoisomer" refers to both enantiomers and diastereomers.

The abbreviation "RT" means room temperature.

The abbreviation "hr" or "h" means hour(s).

The abbreviation "DCM" means dichloromethane.

Throughout this specification, a variable may be referred to generally (e.g., "each R") or may be referred to specifically, or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present disclosure provides a compound of Formula A:

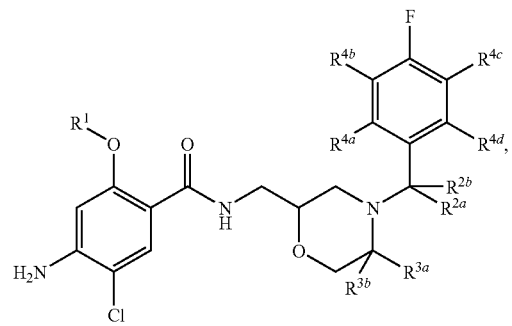

or a pharmaceutically acceptable salt, hydrate or solvate thereof, wherein:

$R^1$ is ethyl wherein from 1 to 5 hydrogen atoms are optionally replaced with deuterium; and each of $R^{2a}$, $R^{2b}$, $R^{3a}$, $R^{3b}$, $R^{4a}$, $R^{4b}$, $R^{4c}$, and $R^{4d}$ is independently selected from H and D; and at least one R comprises a deuterium atom.

In certain embodiments of Formula A:

a) $R^1$ is selected from $—CH_2CH_3$, $—CH_2CD_3$, $—CD_2CH_3$, and $—CD_2CD_3$;

b) each $R^2$ is the same;

c) each $R^3$ is the same; or d) each $R^4$ is the same.

In more specific embodiments, a compound of Formula A has the features set forth in two or more of a) through d), above.

In another specific embodiment, each $R^4$ in a compound of Formula A is deuterium. In an even more specific embodiment, each $R^4$ in a compound of Formula A is deuterium and the compound has the features set forth in one or more of a) through c), above.

An even more specific embodiment of Formula A is the compound:

Compound 112

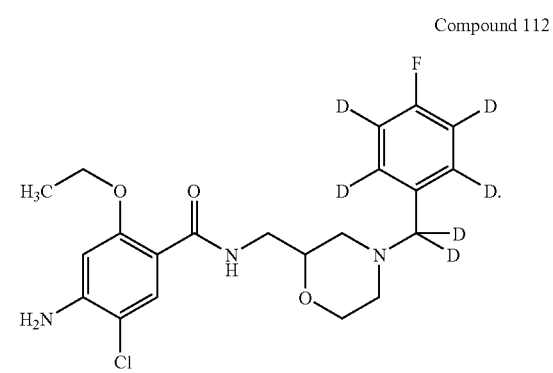

In an alternate embodiment each R⁴ in a compound of Formula A is hydrogen, the compound having the Formula:

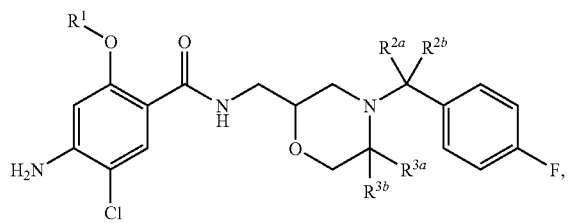

(I)

or a pharmaceutically acceptable salt, hydrate or solvate thereof, wherein:
R¹ is —$CH_nD_{(2-n)}$-$CH_mD_{(3-m)}$;
n is selected from 0, 1 and 2;
m is selected from 0, 1, 2 and 3;
each of $R^{2a}$, $R^{2b}$, $R^{3a}$ and $R^{3b}$ is independently selected from H and D; and at least one R comprises a deuterium atom.

In one embodiment of Formula I, R¹ is —$CD_2$-$CH_mD_{(3-m)}$.

In another embodiment of Formula I, m is selected from 0 and 3. In a more specific embodiment of Formula I, m is 0.

In still another embodiment of Formula I, $R^{2a}$ and $R^{2b}$ are simultaneously H or D; and $R^{3a}$ and $R^{3b}$ are simultaneously H or D. In a more specific embodiment of Formula I, $R^{2a}$ and $R^{2b}$ are simultaneously D. In another specific embodiment of Formula I, $R^{3a}$ and $R^{3b}$ are simultaneously D.

In still another embodiment, the compound is selected from any one of the compounds set forth in Table 1:

TABLE 1

Specific Embodiments of Formula I

| Cmpd | R¹ | $R^{2a}$ | $R^{2b}$ | $R^{3a}$ | $R^{3b}$ |
|------|------|---|---|---|---|
| 100 | $CD_2CH_3$ | D | D | H | H |
| 101 | $CD_2CD_3$ | D | D | H | H |
| 102 | $CD_2CH_3$ | H | H | D | D |
| 103 | $CD_2CD_3$ | H | H | D | D |
| 104 | $CD_2CH_3$ | D | D | D | D |
| 105 | $CD_2CD_3$ | D | D | D | D |
| 106 | $CH_2CH_3$ | D | D | H | H |
| 107 | $CH_2CD_3$ | D | D | H | H |
| 108 | $CH_2CH_3$ | H | H | D | D |
| 109 | $CH_2CD_3$ | H | H | D | D |
| 110 | $CH_2CH_3$ | D | D | D | D |
| 111 | $CH_2CD_3$ | D | D | D | D |

In an even more specific embodiment, the compound of Formula I is:

Compound 106

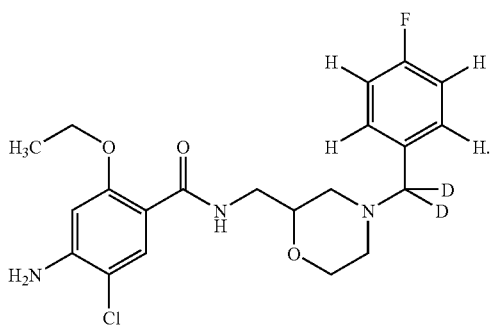

In another embodiment, any atom not designated as deuterium in any of the embodiments set forth above is present at its natural isotopic abundance.

In another set of embodiments, the compound of Formula A or Formula I is isolated or purified, e.g., the compound of Formula A or Formula I is present at a purity of at least 50% by weight (e.g., at least 55%, 60%, 65%, 70%, 75%, 80%, 85%, 90%, 95%, 97%, 98%, 98.5%, 99%, 99.5% or 99.9%) of the total amount of isotopologues of Formula A or Formula I present, respectively. Thus, in some embodiments, a composition comprising a compound of Formula A or Formula I can include a distribution of isotopologues of the compound, provided at least 50% of the isotopologues by weight are the recited compound.

In some embodiments, any position in the compound of Formula A or Formula I designated as having D has a minimum deuterium incorporation of at least 45% (e.g., at least 52.5%, at least 60%, at least 67.5%, at least 75%, at least 82.5%, at least 90%, at least 95%, at least 97%, at least 99%, or at least 99.5%) at the designated position(s) of the compound of Formula A or Formula I. Thus, in some embodiments, a composition comprising a compound of Formula A or Formula I can include a distribution of isotopologues of the compound, provided at least 45% of the isotopologues include a D at the designated position(s).

In some embodiments, a compound of Formula A or Formula I is "substantially free of" other isotopologues of the compound, e.g., less than 50%, less than 25%, less than 10%, less than 5%, less than 2%, less than 1%, or less than 0.5% of other isotopologues are present.

The synthesis of compounds of Formula A or Formula I can be readily achieved by synthetic chemists of ordinary skill. Relevant procedures and intermediates are disclosed, for instance in EP243959.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Each of the patents, patent applications, and publications, whether in traditional journals or available only through the internet, referred to herein, is incorporated in its entirety by reference.

Exemplary Synthesis

A convenient method for synthesizing compounds of Formula A or Formula I are depicted in Schemes Ia-III.

Scheme Ia. Synthesis of Intermediate XIII.

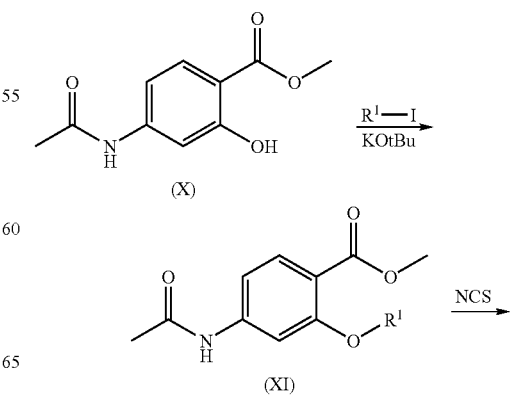

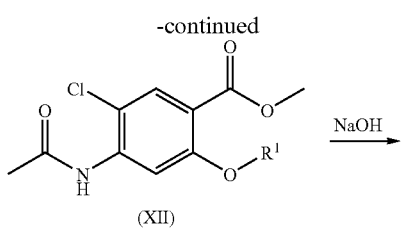

(XII)

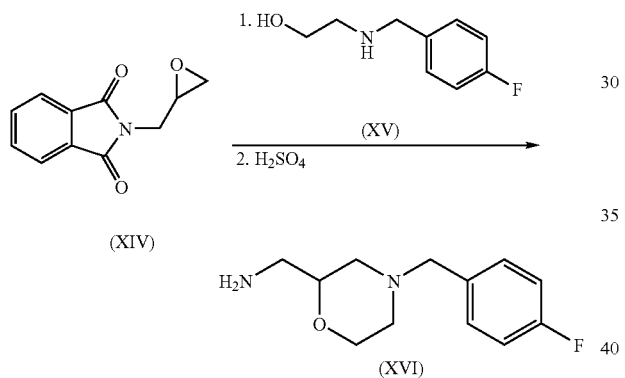

As depicted in Scheme Ia, methyl-4-acetylamino-2-hydroxybenzoate (X) is converted to XI using appropriately deuterated ethyl iodide in the presence of KOtBu. Chlorination of XI with NCS affords XII which is then subjected to alkaline hydrolysis to produce XIII.

As depicted in Scheme Ib, reaction of XIV with XV followed by treatment with conc. $H_2SO_4$ affords XVI.

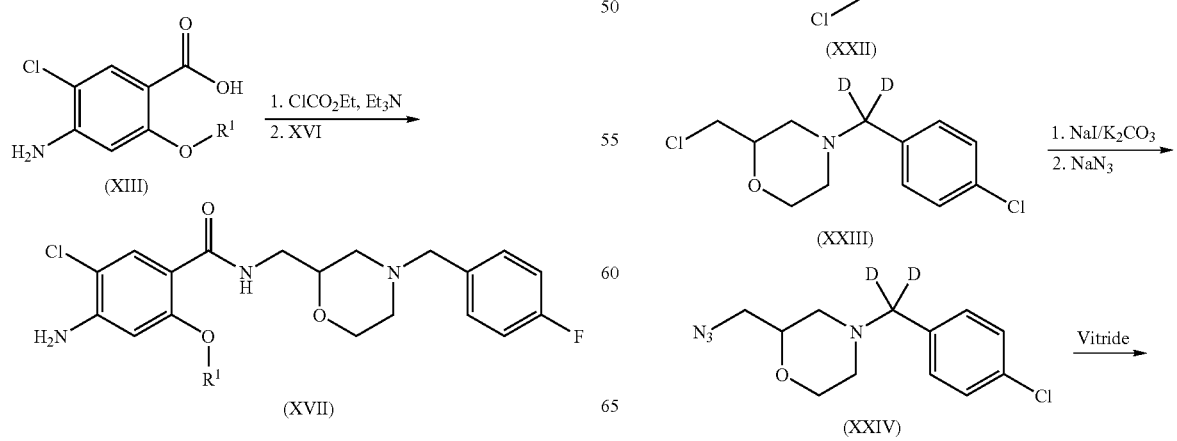

As depicted in Scheme Ic, coupling of XIII to XVI using ethylchloroformate and triethylamine in $CHCl_3$ gives the desired compound (XVII). See, e.g., Kato, S et al, J Med Chem, 1991, 34(2):616; and Kato, S et al, J Med Chem 1990, 33(5):1406.

Scheme II. Synthesis of Compound XXVII
(Formula I; $R^{2a}$, $R^{2b}$ = D; $R^{3a}$, $R^{3b}$ = H)

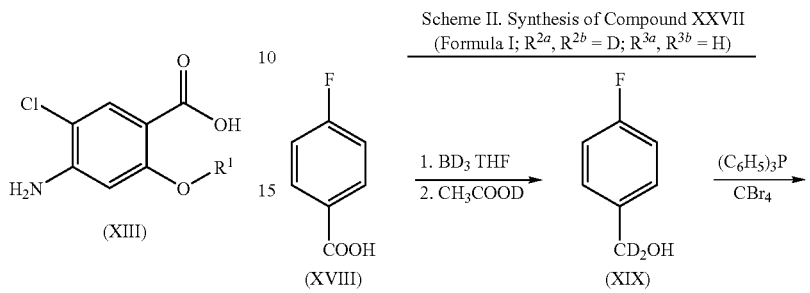

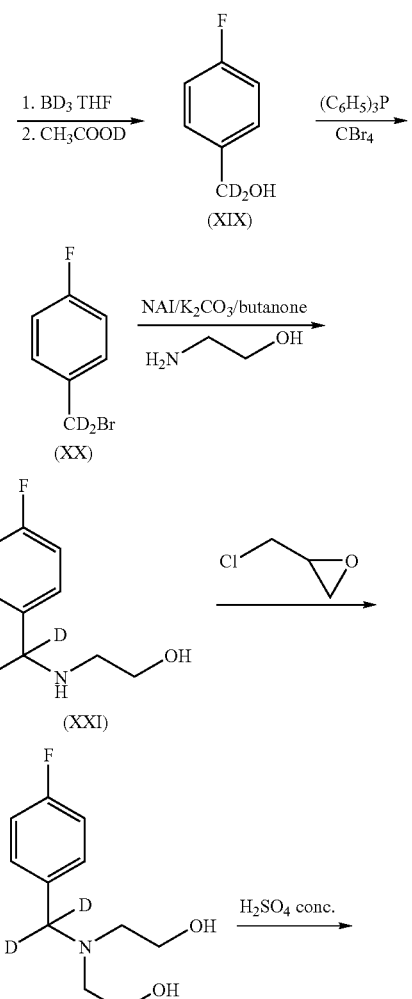

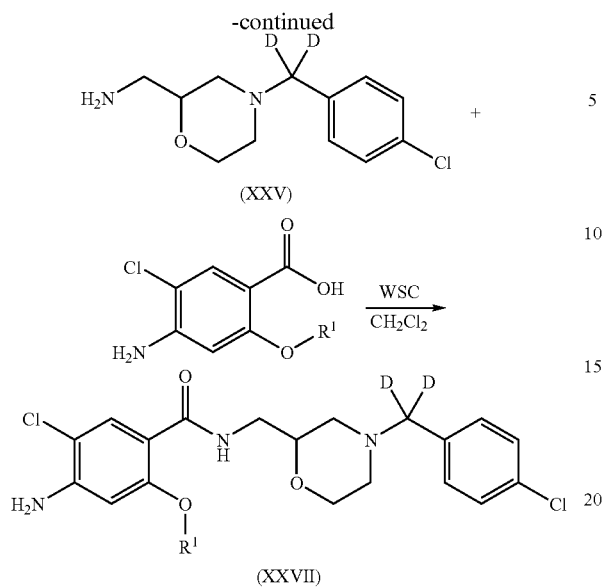

Compound XVIII is treated with $BD_3$ THF and after reduction is quenched with deuterated acetic acid to afford XIX. Treatment with triphenylphosphine/$CBr_4$ affords XX. The bromide adduct (XX) is then reacted with $NaI/K_2CO_3$/ethanolamine to produce XXI. Compound XXI is then reacted with epichlorohydrin to afford XXII, which is then treated with concentrated $H_2SO_4$ to afford the morpholino derivative (XXIII). XXIII is then converted into the azide derivative (XXIV) by reaction with $NaI/K_2CO_3/NaN_3$. Vitride (bis-(2-methoxyethoxy)aluminum hydride reduction of XXIV affords XXV. Coupling of XXV to XIII by means of 1-[3-(dimethylamino)propyl]-3-ethylcarbodiimide (WSC) in $CH_2Cl_2$ gives the desired product (XXVII). See, e.g., Morie, T et al, *J Chem Pharm Bull* 1994, 42(4):877.

Scheme III. Synthesis of Compound XL
(Formula I; $R^{2a}$, $R^{2b}$ = H, $R^{3a}$, $R^{3b}$ = D)

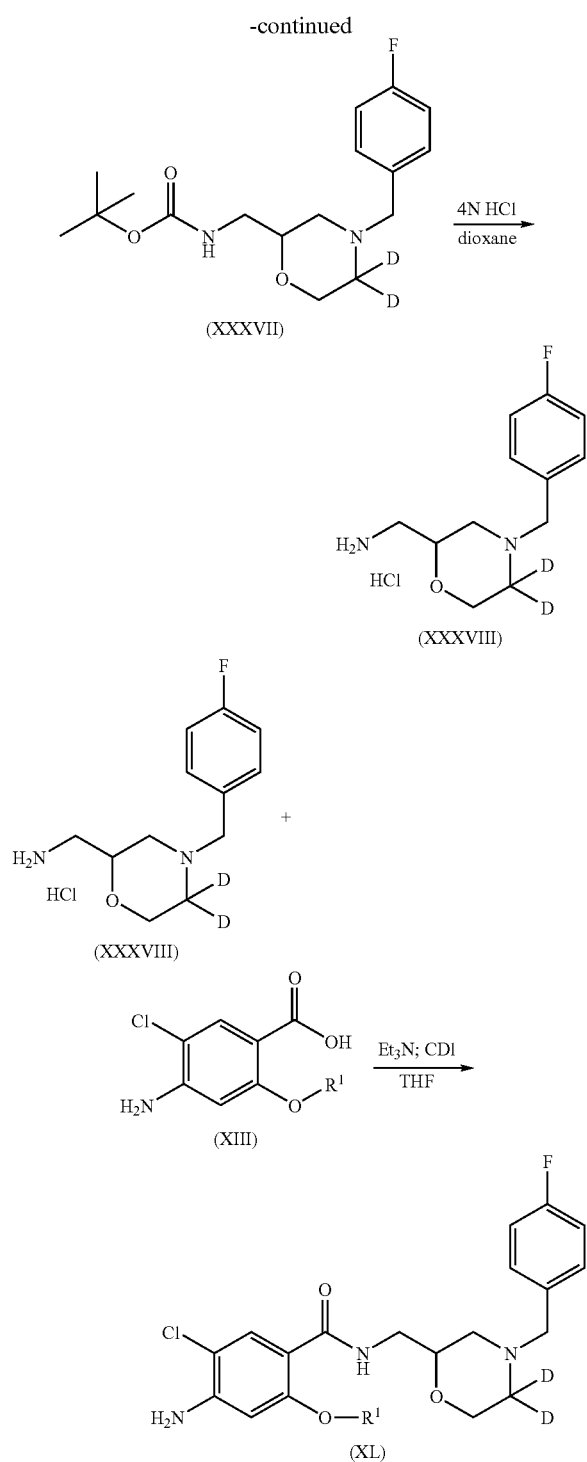

via treatment with $BD_3$ $(CH_3)_2S$ in refluxing THF. After reduction, XXXVI is then reacted with 4-fluorobenzyl bromide and $NaI/K_2CO_3/DMF$ to afford XXXVII which is then deprotected to give compound XXXVIII. Compounds XXXVIII and XXXIX are then coupled via the use of carbonyl diimidazole (CDI) to afford the desired product (XL). Alternatively, XXXVI may be reacted with XX and $NaI/K_2CO_3/DMF$ to afford a tetradeuterated version of XXXVII that can then be utilized as an alternative intermediate in Scheme 3. See, e.g., Kato, S et al, Chem Pharm Bull 1995, 43(4):699.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^{2a}$, $R^{2b}$, $R^{3a}$, $R^{3b}$) or not. The suitability of a chemical group in a compound structure for use in the synthesis of another compound is within the knowledge of one of ordinary skill in the art.

Additional methods of synthesizing compounds of Formula A and Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, $3^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this disclosure are only those that result in the formation of stable compounds.

Compositions

The disclosure also provides pyrogen-free compositions comprising an effective amount of a compound of Formula A or Formula I (e.g., including any of the formulae herein), or a pharmaceutically acceptable salt, solvate, or hydrate of the compound; and an acceptable carrier. Preferably, a composition of this disclosure is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Reaction of compound XXVIII with dibenzylamine XXIX at 80° C. affords alcohol XXX. Treatment of XXX with refluxing concentrated HCl gives the amine XXXI. Acylation of XXXI with chloroacetyl chloride in $CHCl_3$ affords XXXII, which is then cyclized after treatment with KOtBu in refluxing ethanol to afford the morpholine derivative XXXIII. Hydrogenation of XXXIII using Pearlman's catalyst [Pd(OH)$_2$] in ethanol affords XXXIV. Boc protection of the primary amine gave XXXV, which is then reduced to XXXVI If required, the solubility and bioavailability of the compounds of the present disclosure in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this disclosure optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the disclosure include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present disclosure suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this disclosure is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the patient therapeutics may be local, so as to be administered at the site of interest. Various techniques can be used for providing the patient compositions at the site of interest, such as injection, use of catheters, trocars, projectiles, pluronic gel, stents, sustained drug release polymers or other device which provides for internal access.

Thus, according to yet another embodiment, the compounds of this disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the disclosure provides a method of coating an implantable medical device comprising the step of contacting the device with the coating composition described above. It will be obvious to those skilled in the art that the coating of the device will occur prior to implantation into a mammal.

According to another embodiment, the disclosure provides a method of impregnating an implantable drug release device comprising the step of contacting the drug release device with a compound or composition of this disclosure. Implantable drug release devices include, but are not limited to, biodegradable polymer capsules or bullets, non-degradable, diffusible polymer capsules and biodegradable polymer wafers.

According to another embodiment, the disclosure provides an implantable medical device coated with a compound or a composition comprising a compound of this disclosure, such that the compound is therapeutically active.

According to another embodiment, the disclosure provides an implantable drug release device impregnated with or containing a compound or a composition comprising a compound of this disclosure, such that the compound is released from the device and is therapeutically active.

Where an organ or tissue is accessible because of removal from the patient, such organ or tissue may be bathed in a medium containing a composition of this disclosure, a composition of this disclosure may be painted onto the organ, or a composition of this disclosure may be applied in any other convenient way.

In another embodiment, a composition of this disclosure further comprises a second therapeutic agent. The second therapeutic agent may be selected from any compound or therapeutic agent known to have or that demonstrates advantageous properties when administered with a compound having the same mechanism of action as mosapride. Such agents include those indicated as being useful in combination with mosapride, including but not limited to, those described in US2005239845, U.S. Pat. No. 6,676,933, and WO2006011159.

Preferably, the second therapeutic agent is an agent useful in the treatment or prevention of a disease or condition selected from chronic gastritis; heartburn; nausea and vomiting; GI dumping syndrome or post-gastrectomy syndrome; duodenal ulcer; gastric ulcer disease; poorly responsive GERD; erosive esophagitis; pathological gastrointestinal hypersecretory disease; Zollinger Ellison Syndrome; esophageal disorder; acid dyspepsia; Parkinson's disease induced constipation; type 2 Diabetes mellitus; and gastroparesis.

In one embodiment, the second therapeutic agent is selected from a proton pump inhibitor, such as pantoprazole, omeprazole, and Rabeprazole; an H2 antagonist, such as famotidine; an anti-flatulent, such as methylpolysiloxane and simethicone; and pancreatin.

In another embodiment, the disclosure provides separate dosage forms of a compound of this disclosure and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the disclosure, the compound of the present disclosure is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this disclosure can range from 5-10 mg/day/average adult human; 1-50 mg/day/average adult human; or 0.1-75 mg/day/average adult human.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for mosapride.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this disclosure. When this occurs, it will allow the effective dosage of the second therapeutic agent and/or the compound of this disclosure to be reduced from that required in a monotherapy. This has the advantage of minimizing toxic side effects of either the second therapeutic agent of a compound of this disclosure, synergistic improvements in efficacy, improved ease of administration or use and/or reduced overall expense of compound preparation or formulation.

Methods of Treatment

In another embodiment, the disclosure provides a method of modulating the activity of 5HT4 serotonin receptor agonist in a cell, comprising contacting a cell with one or more compounds of Formula A or Formula I herein.

According to another embodiment, the disclosure provides a method of treating a patient suffering from, or susceptible to, a disease that is beneficially treated by mosapride comprising the step of administering to the patient an effective amount of a compound or a composition of this disclosure. Such diseases are well known in the art and are disclosed in, but not limited to the following patents and published applications: EP243959; US2005239845; and WO2005004865.

In one particular embodiment, the method of this disclosure is used to treat a patient suffering from or susceptible to a disease or condition selected from GI dumping syndrome or post-gastrectomy syndrome, constipation in patients with Parkinson's Disease; gastroparesis, and in patients with Type-2 Diabetes mellitus; chronic gastritis, heartburn, nausea and vomiting, and gastroesophageal reflux disease (GERD).

In another particular embodiment, the method of this disclosure is used to treat a patient suffering from or susceptible to a disease or condition selected from chronic gastritis, heartburn, nausea and vomiting, and gastroesophageal reflux disease (GERD).

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to the patient one or more second therapeutic agents. The choice of second therapeutic agent may be made from any second therapeutic agent known to be useful for co-administration with mosapride. The choice of second therapeutic agent is also dependent upon the particular disease or condition to be treated. Examples of second therapeutic agents that may be employed in the methods of this disclosure are those set forth above for use in combination compositions comprising a compound of this disclosure and a second therapeutic agent.

In particular, the combination therapies of this disclosure include treating a patient suffering from a gastrointestinal disorder comprising the step of co-administering a compound of Formula A or Formula I and a second therapeutic agent selected from a proton pump inhibitor, such as pantoprazole, omeprazole, and Rabeprazole; an H2 antagonist, such as famotidine; an anti-flatulent, such as methylpolysiloxane and simethicone; and pancreatin.

The term "co-administered" as used herein means that the second therapeutic agent may be administered together with a compound of this disclosure as part of a single dosage form (such as a composition of this disclosure comprising a compound of the disclosure and an second therapeutic agent as described above) or as separate, multiple dosage forms. Alternatively, the additional agent may be administered prior to, consecutively with, or following the administration of a compound of this disclosure. In such combination therapy treatment, both the compounds of this disclosure and the second therapeutic agent(s) are administered by conventional methods. The administration of a composition of this disclosure, comprising both a compound of the disclosure and a second therapeutic agent, to a patient does not preclude the separate administration of that same therapeutic agent, any other second therapeutic agent or any compound of this disclosure to the patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the disclosure, where a second therapeutic agent is administered to a patient, the effective amount of the compound of this disclosure is less than its effective amount would be where the second therapeutic agent is not administered. In another embodiment, the effective amount of the second therapeutic agent is less than its effective amount would be where the compound of this disclosure is not administered. In this way, undesired side effects associated with high doses of either agent may be minimized. Other potential advantages (including without limitation improved dosing regimens and/or reduced drug cost) will be apparent to those of skill in the art. In yet another aspect, the disclosure provides the use of a compound of Formula A or Formula I alone or together with one or more of the above-described second therapeutic agents in the manufacture of a medicament, either as a single composition or as separate dosage forms, for treatment or prevention in a patient of a disease, disorder or symptom set forth above. Another aspect of the disclosure is a compound of Formula A or Formula I for use in the treatment or prevention in a patient of a disease, disorder or symptom thereof delineated herein.

EXAMPLES

Example 1

Synthesis of 4-fluorobenz(aldehyde-d$_1$) (12)

Intermediate 12 was prepared according to Scheme IV below. Details of the synthesis are set forth below.

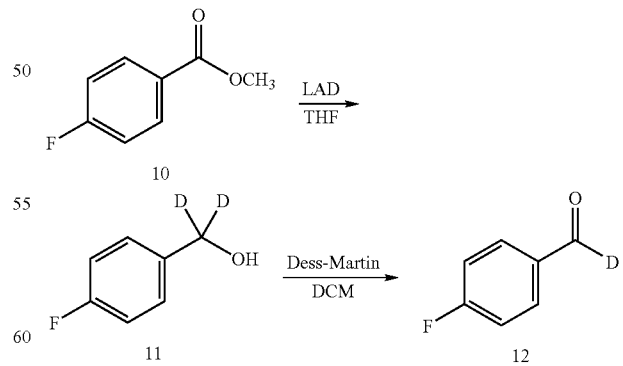

Scheme IV: Synthesis of Intermediate 12.

Synthesis of (4-fluorophenyl)methanol-d$_2$ (11)

To a suspension of LAD (0.272 g, 6.5 mmol, 1 equiv) in THF (10 mL) at 78° C., was added methyl 4-fluorobenzoate 10 (1.00 g, 6.5 mmol) with stirring. After stirring 1 h at 78° C., the reaction was quenched by the addition of MgSO$_4$.7H$_2$O. The reaction mixture was filtered to remove solids and the filtrate was concentrated in vacuo to yield 11 as a white solid (0.565 g).

Synthesis of 4-fluorobenz(aldehyde-d$_1$) (12)

To a solution of alcohol 11 (0.565 g, 4.4 mmol) in DCM (15 mL) was added Dess-Martin periodinane (2.805 g, 6.6 mmol, 1.5 equiv) at RT with stirring. The reaction mixture was stirred at RT overnight then was washed with saturated NaHCO$_3$ solution (15 mL) followed by saturated Na$_2$S$_2$O$_3$ solution (15 mL). The combined aqueous layers were extracted with DCM (15 mL) and the organic layers were combined and concentrated under reduced pressure, then further dried under high vacuum to yield aldehyde 12 (1.63 mg).

Example 2

Synthesis of 4-fluoro-2,3,5,6-d$_4$-benz(aldehyde-d$_1$) (16)

Intermediate 16 was prepared as outlined in Scheme V below. Details of the synthesis are set forth below.

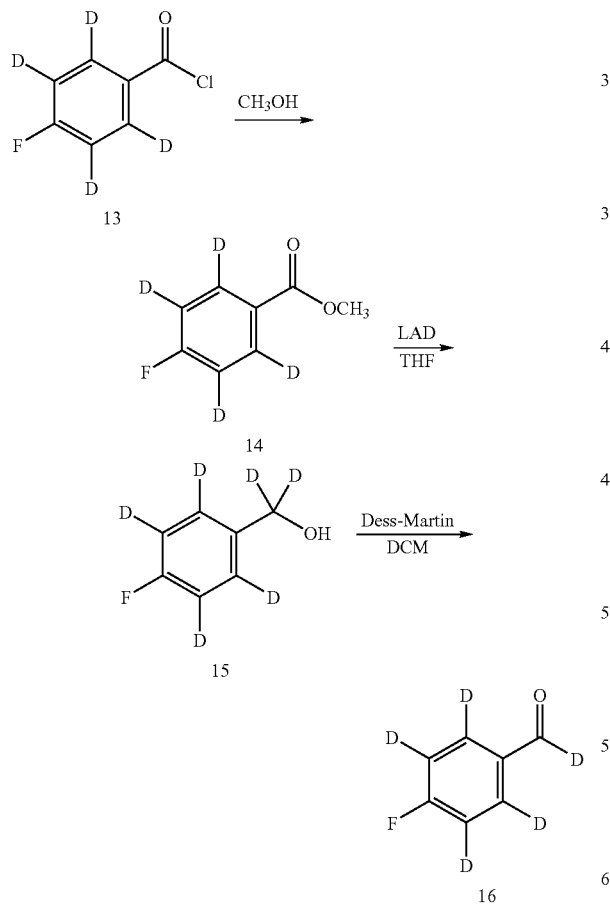

Synthesis of methyl (4-fluoro-2,3,5,6-d$_4$-phenyl) methanol-d$_2$ (15).

A solution of acid chloride 13 (3.00 g, 18.5 mmol) in CH$_3$OH (30 mL) was stirred for 30 minutes at RT then concentrated in vacuo to afford the methyl ester 14 (3.3 g, 20.9 mmol). A slurry of LAD (0.964 g, 23.0 mmol, 1.2 equiv) in THF (30 mL) was stirred and cooled to 78° C. followed by addition of the ester 14. After stirring at RT overnight, the reaction was quenched by the dropwise addition of 964 μL H$_2$O, followed by 964 μL of 15% NaOH, and finally 2.892 mL of H$_2$O. The precipitate was removed by filtration and washed with THF. The combined organic layers were dried over Na$_2$SO$_4$, and concentrated in vacuo to yield product 15 (2.13 g).

Synthesis of 4-fluoro-2,3,5,6-d$_4$-benz(aldehyde-d$_1$) (16)

To a solution of alcohol 15 (2.13 g, 16.1 mmol) in DCM (30 mL) was added Dess-Martin periodinane (10.25 g, 24.2 mmol, 1.5 equiv) at RT with stirring. The reaction mixture was stirred overnight at RT under N$_2$ then was washed consecutively with saturated NaHCO$_3$ solution and saturated NaS$_2$O$_3$ solution. The combined aqueous layers were extracted with DCM (30 mL), then the combined organic layers were dried over Na$_2$SO$_4$, filtered and concentrated in vacuo to yield aldehyde 16 (120 mg).

Example 3

Synthesis of 4-amino-5-chloro-2-ethoxy-N-(morpholin-2-ylmethyl)benzamide (21)

Intermediate 21 was prepared as outlined in Scheme VI below. Details of the synthesis are set forth below.

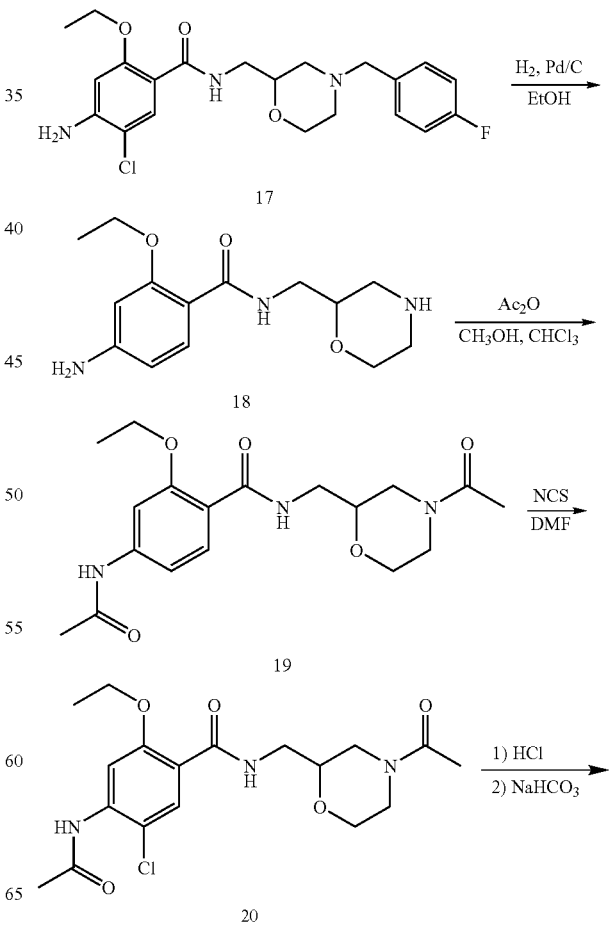

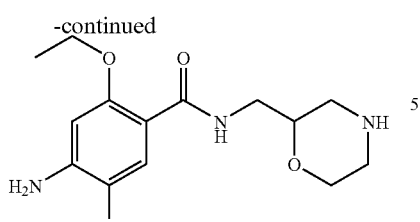

21

Synthesis of 4-amino-2-ethoxy-N-(morpholin-2-ylmethyl)benzamide (18)

A suspension of commercially available benzamide 17 (3.00 g, 7.1 mmol) in EtOH (75 mL) was purged with $N_2$, followed by the addition of Pd/C (38 mg, 0.355 mmol, 0.05 equiv). The $N_2$ atmosphere was evacuated and replaced by $H_2$ and the resulting mixture was stirred overnight. Due to incomplete conversion, additional Pd/C (800 mg) was added to the flask and stirring at RT under $H_2$ was continued overnight. After this time, due to incomplete conversion, acetic acid (6 mL) was added and stirring of the reaction mixture at 50° C. under $H_2$ was continued overnight. The catalyst was removed by filtration and the filtrate was concentrated in vacuo to a yellow oil. The oil was dissolved in water then made basic by the addition of 10% NaOH. The resulting precipitate was filtered, washed with $H_2O$ then dried under vacuum to yield product 18 (1.78 g).

Synthesis of 4-acetamido-N-((4-acetylmorpholin-2-yl)methyl)-2-ethoxybenzamide (19)

To a solution of 18 (1.20 g, 4.3 mmol) in $CH_3OH$ (50 mL) and $CHCl_3$ (12.5 mL) was added acetic anhydride (0.897 mL, 9.5 mmol, 2.21 equiv) at RT with stirring. The reaction mixture was stirred at RT overnight after which time the solvent was removed in vacuo and the resulting residue was dissolved in $CHCl_3$. The organic solution was washed consecutively with 10% NaOH, water, then brine, then was concentrated under reduced pressure to yield 19 as a white solid (1.78 g).

Synthesis of 4-acetamido-N-((4-acetylmorpholin-2-yl)methyl)-5-chloro-2-ethoxybenzamide (20)

A solution of 19 (1.78 g, 4.9 mmol) and N-chlorosuccinimide (0.687 g, 5.1 mmol, 1.05 equiv) in DMF (30 mL) was stirred for 1 h at 70° C. The reaction mixture was then concentrated under reduced pressure to dryness. The residue was triturated with $H_2O$ and the resulting solids were removed by filtration and recrystallized from $CH_3OH$ to yield 20 (1.314 g).

Synthesis of 4-amino-5-chloro-2-ethoxy-N-(morpholin-2-ylmethyl)benzamide (21)

A suspension of 20 (1.314 g, 3.3 mmol) in 10% HCl (25 mL) was stirred under reflux conditions for 3 h. The mixture was cooled to 0° C., and the resulting precipitate was collected and dried by suction filtration to afford the dihydrochloride salt of 21 (481 mg). Prior to use, the dihydrochloride salt of 21 was dissolved in saturated $NaHCO_3$ solution with stirring, the mixture was extracted with DCM, and the organic was dried over $Na_2SO_4$ and concentrated in vacuo to yield the free base 21.

Example 4

Synthesis of 4-amino-5-chloro-2-ethoxy-N-((4-(4-fluorobenzyl)morpholin-2-yl)methyl-$d_2$)benzamide (106)

Compound 106 was prepared as outlined in Scheme VII below. Details of the synthesis are set forth below.

Scheme VII: Synthesis of Compound 106.

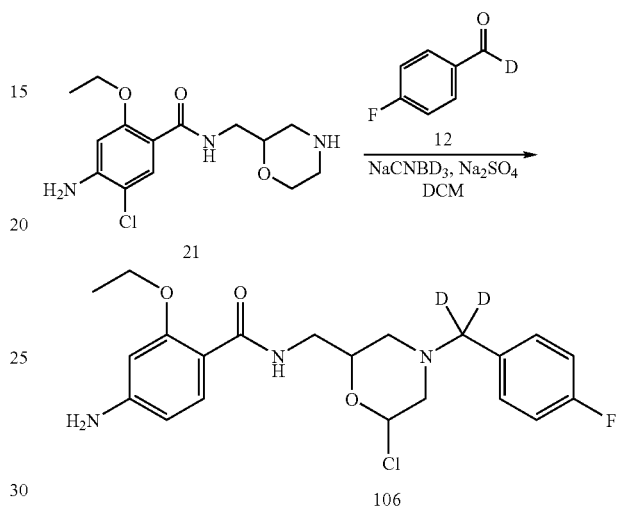

Synthesis of 4-amino-5-chloro-2-ethoxy-N-((4-(4-fluorobenzyl)morpholin-2-yl)methyl-$d_2$)benzamide (106)

To a solution of 21 (0.326 g, 1.0 mmol) in DCM (30 mL) was added $Na_2SO_4$ (for drying purposes) followed by aldehyde 12 (0.156 g, 1.2 mmol, 1.2 equiv). The mixture was stirred at RT under $N_2$ for 30 minutes, then $NaCNBD_3$ (0.082 g, 1.2 mmol, 1.2 equiv) was added and stirring was continued overnight at RT. The reaction was quenched by the addition of $NaHCO_3$ solution and the resulting mixture was extracted with EtOAc (2×20 mL). The combined organic layers were dried over $Na_2SO_4$, concentrated in vacuo, and the resulting crude material was purified by automated flash column chromatography (0-10% MeOH/DCM) to yield pure final product 106 (52 mg). $^1$H-NMR (300 MHz, $CDCl_3$): δ 1.48 (t, J=7.0, 3H), 1.98 (t, J=10.7, 1H), 2.16 (td, $J_1$=11.0, $J_2$=3.0, 1H), 2.63 (d, J=11.5, 1H), 2.75 (d, J=11.3, 1H), 3.30-3.36 (m, 1H), 3.64-3.72 (m, 3H), 3.85-3.88 (m, 1H), 4.07 (q, J=7.0, 2H), 4.34 (s, 2H), 6.26 (s, 1H), 7.00 (t, J=8.5, 2H), 7.26 (partially obscured by $CHCl_3$, t, J=8.5, 2H), 8.11 (s, 1H), 8.19-8.23 (m, 1H). HPLC (method: 150 mm C18-RP column—gradient method 5-95% ACN; Wavelength: 254 nm): retention time: 3.19 min. MS (M+H): 424.2.

Example 5

Synthesis of 4-amino-5-chloro-2-ethoxy-N-((4-(4-fluoro-2,3,5,6-$d_4$-benzyl-)morpholin-2-yl)methyl-$d_2$)benzamide (112)

Compound 112 was prepared in a manner similar to that outlined in Scheme VII above. Details of the synthesis are set forth below.

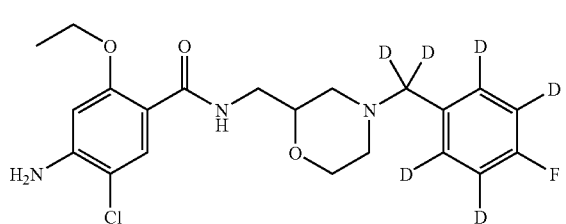

Synthesis of 4-amino-5-chloro-2-ethoxy-N-((4-(4-fluorobenzyl-d₄)morpholin-2-yl)methyl-d₂)benzamide (112)

To a solution of 21 (0.230 g, 0.7 mmol) in DCM (20 mL) was added $Na_2SO_4$ (for drying purposes) and aldehyde 16 (0.114 g, 0.9 mmol, 1.2 equiv) with stirring at RT. The mixture was stirred at RT under $N_2$ for 30 min, then $NaCNBD_3$ (0.058 g, 0.9 mmol, 1.2 equiv) was added and stirring was continued overnight at RT. The reaction was quenched by the addition of saturated $NaHCO_3$ solution and the resulting mixture was extracted with EtOAc (2×15 mL). The combined organic layers were dried over $Na_2SO_4$ and concentrated in vacuo. The resulting crude material was purified via automated reverse phase flash column chromatography (0-100% $ACN/H_2O$) to yield pure final product 112 (48 mg). $^1$H-NMR (300 MHz, $CDCl_3$): δ 1.49 (t, J=7.0, 3H), 1.98 (t, J=10.7, 1H), 2.16 (td, $J_1$=11.3, $J_2$=3.3, 1H), 2.63 (d, J=11.1, 1H), 2.75 (d, J=11.0, 1H), 3.30-3.36 (m, 1H), 3.63-3.71 (m, 3H), 3.85-3.90 (m, 1H), 4.07 (q, J=7.0, 2H), 4.32 (s, 2H), 6.26 (s, 1H), 8.11 (s, 1H), 8.20-8.23 (m, 1H). HPLC (method: 150 mm C18-RP column—gradient method 5-95% ACN; Wavelength: 254 nm): retention time: 2.99 min. MS (M+H): 428.1.

Diagnostic Methods and Kits

The compounds and compositions of this disclosure are also useful as reagents in methods for determining the concentration of mosapride in solution or biological sample such as plasma, examining the metabolism of mosapride and other analytical studies.

According to one embodiment, the disclosure provides a method of determining the concentration, in a solution or a biological sample, of mosapride, comprising the steps of:
 a) adding a known concentration of a compound of Formula A or Formula I to the solution of biological sample;
 b) subjecting the solution or biological sample to a measuring device that distinguishes mosapride from a compound of Formula I or Formula A;
 c) calibrating the measuring device to correlate the detected quantity of the compound of Formula I with the known concentration of the compound of Formula I or Formula A added to the biological sample or solution; and
 d) measuring the quantity of mosapride in the biological sample with the calibrated measuring device; and
 e) determining the concentration of mosapride in the solution of sample using the correlation between detected quantity and concentration obtained for a compound of Formula I or Formula A.

Measuring devices that can distinguish mosapride from the corresponding compound of Formula I or Formula A include any measuring device that can distinguish between two compounds that differ from one another in isotopic abundance.

Exemplary measuring devices include a mass spectrometer, NMR spectrometer, or IR spectrometer.

In another embodiment, a method for determining the amount of mosapride in a solution or a biological sample is provided, comprising:
 a) adding a known amount of a compound of Formula A or Formula I to the solution or biological sample;
 b) detecting at least one signal for a compound of Formula A or Formula I and at least one signal for mosapride in a measuring device that is capable of distinguishing the two compounds;
 c) correlating the at least one signal detected for a compound of Formula A or Formula I with the known amount of the compound of Formula A or Formula I added to the solution or the biological sample; and
 d) determining the amount of mosapride in the solution or biological sample using the correlation between the at least one signal detected of the compound of Formula A or Formula I and the amount added to the solution or biological sample of a compound of Formula A or Formula I.

In another embodiment, the disclosure provides a method of evaluating the metabolic stability of a compound of Formula I or Formula A comprising the steps of contacting the compound of Formula I or Formula A with a metabolizing enzyme source for a period of time and comparing the amount of the compound of Formula I or Formula A with the metabolic products of the compound of Formula I or Formula A, respectively, after the period of time.

In a related embodiment, the disclosure provides a method of evaluating the metabolic stability of a compound of Formula I or Formula A in a patient following administration of the compound of Formula I or Formula A. This method comprises the steps of obtaining a serum, blood, plasma, tissue, urine or feces sample from the patient at a period of time following the administration of the compound of Formula I or Formula A to the patient; and comparing the amount of the compound of Formula I or Formula A with the metabolic products of the compound of Formula I or Formula A in the serum, blood, plasma, tissue, urine or feces sample.

The present disclosure also provides kits for use to treat chronic gastritis including heartburn; nausea and vomiting; gastroesophageal reflux disease (GERD); GI dumping syndrome or post-gastrectomy syndrome; constipation in patients with Parkinson's disease; patients with Type-2 Diabetes mellitus; and gastroparesis. These kits comprise (a) a pharmaceutical composition comprising a compound of Formula I or Formula A, or a salt, hydrate, or solvate thereof, wherein the pharmaceutical composition is in a container; and (b) instructions describing a method of using the pharmaceutical composition to treat chronic gastritis including heartburn; nausea and vomiting; and gastroesophageal reflux disease (GERD); GI dumping syndrome or post-gastrectomy syndrome; constipation in patients with Parkinson's disease; patients with Type-2 Diabetes mellitus; and gastroparesis.

The container may be any vessel or other sealed or sealable apparatus that can hold the pharmaceutical composition. Examples include bottles, ampules, divided or multi-chambered holders bottles, wherein each division or chamber comprises a single dose of the composition, a divided foil packet wherein each division comprises a single dose of the composition, or a dispenser that dispenses single doses of the composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In on embodiment, the container is a blister pack.

The kits of this disclosure may also comprise a device to administer or to measure out a unit dose of the pharmaceutical composition. Such device may include an inhaler if the composition is an inhalable composition; a syringe and needle if the composition is an injectable composition; a syringe, spoon, pump, or a vessel with or without volume markings if the composition is an oral liquid composition; or any other measuring or delivery device appropriate to the dosage formulation of the composition present in the kit.

In certain embodiment, the kits of this disclosure may comprise in a separate vessel of container a pharmaceutical composition comprising a second therapeutic agent, such as one of those listed above for use for co-administration with a compound of this disclosure.

Evaluation of Metabolic Stability

Certain in vitro liver metabolism studies have been described previously in the following references, each of which is incorporated herein in their entirety: Obach, R. S. *Drug Metab Disp* 1999, 27, p. 1350; Houston, J. B. et al., *Drug Metab Rev* 1997, 29, p. 891; Houston, J. B. *Biochem Pharmacol* 1994, 47, p. 1469; Twatsubo, T et al., *Pharmacol Ther* 1997, 73, p. 147; and Lave, T. et al., *Pharm Res* 1997, 14, p. 152.

Microsomal Assay: The metabolic stability of compounds of Formula A or Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures: Human liver microsomes are obtained from a commercial source (e.g., Absorption Systems L.P. (Exton, Pa.)). The incubation mixtures are prepared as follows:

Reaction Mixture Composition

| | |
|---|---|
| Liver Microsomes | 1.0 mg/mL |
| NADPH | 1 mM |
| Potassium Phosphate, pH 7.4 | 100 mM |
| Magnesium Chloride | 10 mM |
| Test Compound | 1 µM. |

Incubation of Test Compounds with Liver Microsomes: The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 µM. An aliquot of the reaction mixture is prepared as a blank control, by the addition of plain organic solvent (no test compound added). The reaction is initiated by the addition of cofactors (not added to the negative controls), and then incubated in a shaking water bath at 37° C. Aliquots (200 µL) are withdrawn in triplicate at multiple time points (e.g., 0, 15, 30, 60, and 120 minutes) and combined with 800 µL of ice-cold 50/50 acetonitrile/dH$_2$O to terminate the reaction. The positive controls, testosterone and propranolol, as well as mosapride, are each run simultaneously with the test compounds in separate reactions.

All samples are analyzed using LC-MS (or MS/MS). An LC-MRM-MS/MS method is used for metabolic stability. Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

Without further description, it is believed that one of ordinary skill in the art can, using the preceding description and the illustrative examples, make and utilize the compounds of the present disclosure and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the disclosure. All the patents, journal articles and other documents discussed or cited above are herein incorporated by reference.

We claim:

1. A compound of Formula A:

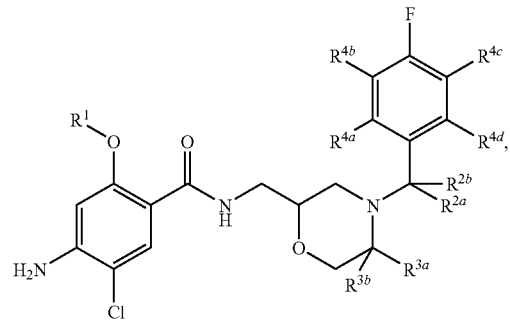

or a pharmaceutically acceptable salt, hydrate or solvate thereof, wherein:

$R^1$ is ethyl wherein from 1 to 5 hydrogen atoms are optionally replaced with deuterium; and each of $R^{2a}$, $R^{2b}$, $R^{3a}$, $R^{3b}$, $R^{4a}$, $R^{4b}$, $R^{4c}$, and $R^{4d}$ is independently selected from H and D; and at least one R comprises a deuterium atom.

2. The compound of claim 1, wherein $R^1$ is selected from —CH$_2$CH$_3$, —CH$_2$CD$_3$, —CD$_2$CH$_3$, and —CD$_2$CD$_3$.

3. The compound of claim 1, wherein each $R^2$ is the same.

4. The compound of any one of claims 1 to 3, wherein each $R^3$ is the same.

5. The compound of any one of claims 1 to 3, wherein each $R^4$ is the same.

6. The compound of claim 5, wherein each $R^4$ is deuterium.

7. The compound of claim 6, wherein the compound is:

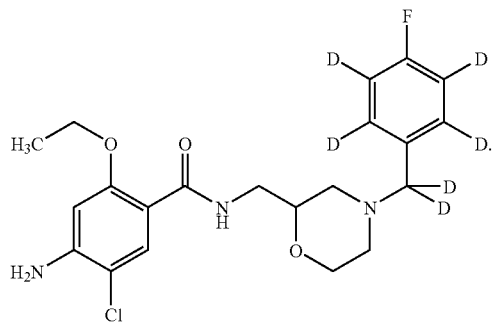

8. The compound of any one of claims 1 to 3, wherein each $R^4$ is deuterium or each $R^4$ is hydrogen.

9. The compound of claim 8, wherein each $R^4$ is hydrogen, and wherein the compound is selected from any one of the compounds set forth in the table below:

| Cmpd | $R^1$ | $R^{2a}$ | $R^{2b}$ | $R^{3a}$ | $R^{3b}$ |
|------|-------|----------|----------|----------|----------|
| 100  | $CD_2CH_3$ | D | D | H | H |
| 101  | $CD_2CD_3$ | D | D | H | H |
| 102  | $CD_2CH_3$ | H | H | D | D |
| 103  | $CD_2CD_3$ | H | H | D | D |
| 104  | $CD_2CH_3$ | D | D | D | D |
| 105  | $CD_2CD_3$ | D | D | D | D |

-continued

| Cmpd | $R^1$ | $R^{2a}$ | $R^{2b}$ | $R^{3a}$ | $R^{3b}$ |
|------|-------|----------|----------|----------|----------|
| 106  | $CH_2CH_3$ | D | D | H | H |
| 107  | $CH_2CD_3$ | D | D | H | H |
| 108  | $CH_2CH_3$ | H | H | D | D |
| 109  | $CH_2CD_3$ | H | H | D | D |
| 110  | $CH_2CH_3$ | D | D | D | D |
| 111  | $CH_2CD_3$ | D | D | D | D |

10. The compound of claim 9, wherein the compound is:

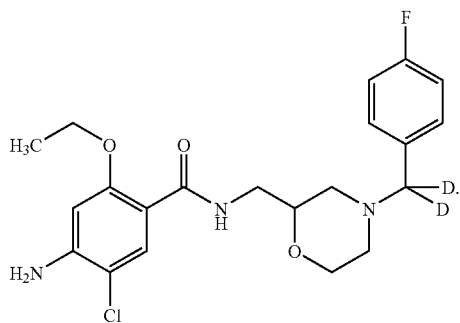

11. The compound according to any one of claims 1 to 3, wherein each atom not designated as deuterium is present at its natural isotopic abundance.

* * * * *

UNITED STATES PATENT AND TRADEMARK OFFICE
CERTIFICATE OF CORRECTION

PATENT NO. : 7,528,131 B2  Page 1 of 1
APPLICATION NO. : 12/106127
DATED : May 5, 2009
INVENTOR(S) : Rose A. Persichetti It is certified that error appears in the above-identified patent and that said Letters Patent is hereby corrected as shown below:

Title Page, item [56] Other Publications, References Cited, Obach reference, please delete "Predictions" and insert --Prediction-- therefor.

Signed and Sealed this

Fourteenth Day of July, 2009

JOHN DOLL
*Acting Director of the United States Patent and Trademark Office*